United States Patent
Li et al.

(10) Patent No.: US 9,274,068 B2
(45) Date of Patent: Mar. 1, 2016

(54) METHODS RELATED TO X-RAY SENSITIVE BATTERY SEPARATORS

(71) Applicant: Celgard, LLC, Charlotte, NC (US)

(72) Inventors: Xuefa Li, Matthews, NC (US); C. Glen Wensley, Rock Hill, SC (US); Zhengming Zhang, Charlotte, NC (US)

(73) Assignee: Celgard LLC, Charlotte, NC (US)

( * ) Notice: Subject to any disclaimer, the term of this patent is extended or adjusted under 35 U.S.C. 154(b) by 0 days.

(21) Appl. No.: 14/859,471

(22) Filed: Sep. 21, 2015

(65) Prior Publication Data
US 2016/0011127 A1    Jan. 14, 2016

Related U.S. Application Data

(62) Division of application No. 12/689,418, filed on Jan. 19, 2010.

(51) Int. Cl.
*G01N 23/18* (2006.01)
*H01M 2/16* (2006.01)

(52) U.S. Cl.
CPC .............. *G01N 23/18* (2013.01); *H01M 2/1646* (2013.01); *H01M 2/1686* (2013.01)

(58) Field of Classification Search
CPC ............................................... G01N 2223/646
See application file for complete search history.

(56) References Cited

U.S. PATENT DOCUMENTS

| | | | |
|---|---|---|---|
| 6,057,061 A | 5/2000 | Callahan et al. | |
| 6,080,507 A | 6/2000 | Yu | |
| 6,368,742 B2 | 4/2002 | Fisher et al. | |
| 6,627,346 B1 * | 9/2003 | Kinouchi | H01M 2/166 429/144 |
| 7,323,274 B1 | 1/2008 | Samii et al. | |
| 2007/0042171 A1 | 2/2007 | Zguris et al. | |
| 2007/0196638 A1 | 8/2007 | Wei et al. | |
| 2009/0081535 A1 | 3/2009 | Zhang | |
| 2009/0117455 A1 | 5/2009 | Takita | |
| 2009/0170005 A1 | 7/2009 | Kimishima et al. | |

FOREIGN PATENT DOCUMENTS

| | | |
|---|---|---|
| JP | 2000-249664 | 9/2000 |
| JP | 2004-156975 | 6/2004 |
| JP | 2008-094911 | 4/2008 |
| JP | 2009-110937 A | 5/2009 |

OTHER PUBLICATIONS

Robert E. Kesting, "Synthetic Polymeric Membranes, A Structural Perspective," 2nd ed., John Wiley & Sons (New York City, NY), (p. 237-286 & 290-297), (1985).

* cited by examiner

*Primary Examiner* — Hoon Song
(74) *Attorney, Agent, or Firm* — Hammer & Associates, P.C.

(57) ABSTRACT

A method for detecting the position of a separator relative to electrodes in a secondary lithium battery includes the steps of: providing a secondary lithium battery including a positive electrode, a negative electrode, a X-ray sensitive separator located between the electrodes, and a can or pouch housing the electrodes and separator, the X-ray sensitive separator comprising a microporous membrane having a X-ray detectable element dispersed therein or thereon, the X-ray detectable element comprising at least 2 and no greater than 20 weight % of the membrane; subjecting the secondary lithium battery to X-ray radiation; determining the position of the separator relative to the electrodes; and approving or rejecting the secondary lithium battery based upon the position of the separator relative to the electrodes.

10 Claims, 1 Drawing Sheet

METHODS RELATED TO X-RAY SENSITIVE BATTERY SEPARATORS

RELATED APPLICATION

This application is a divisional application claiming the benefit of U.S. application Ser. No. 12/689,418 filed Jan. 19, 2010.

FIELD OF INVENTION

The instant application relates to X-ray sensitive or detectable battery separators and methods for making and using such separators, including methods for detecting the position of such a separator in a battery, cell, stack, jellyroll, can, or the like.

BACKGROUND OF THE INVENTION

A battery separator is used to separate the positive and negative electrodes of a battery, for example, in a secondary lithium battery. A battery separator is typically microporous to allow ionic current with least possible resistance while preventing the electrodes from direct contact resulting in an internal short.

In general, a battery separator is sandwiched between the positive electrode and the negative electrode of a secondary lithium battery. It is important for a battery separator to remain in its proper position because even a minute displacement may cause a short in the battery. Currently, other than as described in US Publication US2009/0081535 A1, published Mar. 26, 2009, there are no prevailing techniques to determine the position of a separator in a battery to prevent the introduction of flawed batteries, i.e. those batteries in which the battery separator (or electrode) was displaced during the manufacturing process, into the consumer market.

Microporous polymer membranes are known, can be made by various processes, and the process by which the membrane is made may have an impact upon the membrane's physical attributes. See, for example, Kesting, Robert E., *Synthetic Polymeric Membranes, A Structural Perspective*, Second Edition, John Wiley & Sons, New York, N.Y., (1985). Three different known processes for making microporous polymer membranes include: the dry-stretch process (also known as the CELGARD process), the wet process, and the particle stretch process.

The dry-stretch process (the CELGARD process) refers to a process where pore formation results from stretching a nonporous, semicrystalline, extruded polymer precursor in the machine direction (MD stretch). See, for example, Kesting, Ibid. pages 290-297, incorporated herein by reference. Such a dry-stretch process is different from the wet process and the particle stretch process. Generally, in the wet process, also known as the phase inversion process, the extraction process, or the TIPS process, the polymeric raw material is mixed with a processing oil (sometimes referred to as a plasticizer), this mixture is extruded, and pores are then formed when the processing oil is removed (these films may be stretched before or after the removal of the oil). See, for example, Kesting, Ibid. pages 237-286, incorporated herein by reference.

Generally, in the particle stretch process, the polymeric raw material is mixed with a pore formation particulate, this mixture is extruded, and pores are formed during stretching when the interfaces between the polymer and the particulate fracture due to the stretching forces. See, for example, U.S. Pat. Nos. 6,057,061 and 6,080,507, each incorporated herein by reference.

Moreover, the membranes arising from these different formation processes are usually physically different and the process by which each is made typically distinguishes one membrane from the other. For example, dry-stretch process membranes may have slit shaped pores due to the stretching of the precursor in the machine direction (MD stretch). Wet process membranes tend to have rounder pores and a lacelike appearance due to the oil or plasticizer and the stretching of the precursor in the machine direction (MD stretch) and in the transverse machine direction or transverse direction (TD stretch). Particle stretch process membranes, on the other hand, may have oval shaped pores as the particulate and machine direction stretching (MD stretch) tend to form the pores. Accordingly, each membrane may be distinguished from the other by its method of manufacture.

While membranes made by the dry-stretch process have met with excellent commercial success, such as a variety of Celgard® dry-stretch porous membranes sold by Celgard, LLC of Charlotte, N.C., including flat sheet membranes, battery separators, hollow fibers, and the like, there is a need to improve, modify or enhance at least selected physical attributes thereof, so that they may be used in a wider spectrum of applications, may perform better for particular purposes, or the like.

A modified dry-stretch process (modified CELGARD process) involving the formation of unique round shaped pores by, for example, stretching a nonporous, semicrystalline, extruded polymer precursor in the machine direction (MD stretch), followed by stretching in the transverse direction (TD stretch) with machine direction relax (MD relax) is disclosed in US Published Application US2007/0196638 A1, published Aug. 23, 2007, and incorporated by reference herein.

Despite the research efforts in developing battery separators, there may still be a need for an improved battery separator, such as a battery separator which is x-ray sensitive or readily detectable when inserted or embedded in a battery, cell, stack, jellyroll, can, or the like, to determine its position within the battery, cell, stack, jellyroll, can, or the like, or relative to the electrodes, which is relatively easy to manufacture, is low cost, meets performance requirements, meets product specifications, or the like. Furthermore, there may still be a need for a method for detecting the position of a separator in a battery, cell, stack, jellyroll, can, or the like to determine its position within the battery, cell, stack, jellyroll, can, or the like, or relative to the electrodes, which is relatively easy and cost effective, a method for manufacturing such a separator which is relatively simple and cost effective, a method for using such a separator which is relatively simple and cost effective, or the like.

SUMMARY OF THE INVENTION

A method for detecting the position of a separator relative to electrodes in a secondary lithium battery includes the steps of: providing a secondary lithium battery including a positive electrode, a negative electrode, a X-ray sensitive separator located between the electrodes, and a can or pouch housing the electrodes and separator, the X-ray sensitive separator comprising a microporous membrane having a X-ray detectable element dispersed therein or thereon, the X-ray detectable element comprising at least 2 and no greater than 20 weight % of the membrane; subjecting the secondary lithium battery to X-ray radiation; determining the position of the separator relative to the electrodes; and approving or rejecting the secondary lithium battery based upon the position of the separator relative to the electrodes.

In accordance with at least selected embodiments, the instant application relates to an X-ray sensitive battery separator for a secondary lithium battery and a method for detecting the position of such a separator in a secondary lithium battery. In accordance with at least selected embodiments, the preferred X-ray sensitive battery separator includes a microporous membrane having an X-ray detectable element. In accordance with at least selected embodiments, the X-ray detectable element constitutes a sufficient amount to detect the separator relative to the electrodes (for example, to provide minimum contrast in the x-ray picture). In accordance with at least particular separator embodiments, the X-ray detectable element constitutes less than 20% by weight of the microporous membrane, preferably less than 15% by weight of the microporous membrane, more preferably less than 10% by weight of the microporous membrane, and most preferably less than 5% by weight of the microporous membrane.

At least an exemplary method for detecting the position of a separator in a battery, cell, stack, jellyroll, can, or the like, includes the following steps: (1) providing a battery, cell, stack, jellyroll, can, or the like including an X-ray sensitive or detectable battery separator; (2) subjecting the battery, cell, stack, jellyroll, can, or the like to X-ray radiation; and (3) thereby detecting the position of the separator in the battery, cell, stack, jellyroll, can, or the like.

In accordance with at least selected embodiments of the present invention, there are provided improved battery separators, methods, or the like, such as an improved battery separator which is x-ray sensitive or readily detectable when inserted or embedded in a battery, cell, stack, jellyroll, can, or the like, to determine its position within the battery, cell, stack, jellyroll, can, or the like, or to determine its position relative to the electrodes, which is relatively easy to manufacture, is low cost, meets performance requirements, meets product specifications, and/or the like. Furthermore, in accordance with at least selected embodiments of the present invention, there are provided improved methods for making, using, or detecting the position of a separator in a battery, cell, stack, jellyroll, can, or the like, such as an improved battery separator which is x-ray sensitive or readily detectable, to determine its position within the battery, cell, stack, jellyroll, can, or the like, or relative to the electrodes, which is relatively easy and cost effective, for manufacturing such a separator which is relatively simple and cost effective, for using such a separator which is relatively simple and cost effective, and/or the like.

In accordance with at least certain embodiments, the instant application relates to an X-ray sensitive battery separator for a secondary lithium battery and a method for detecting the position of such a separator in a secondary lithium battery. The X-ray sensitive battery separator preferably includes a microporous membrane having an X-ray detectable element. In at least one embodiment, the X-ray detectable element, such as barium sulfate particles, preferably constitutes less than 5% by weight of the microporous membrane. The method for detecting the position of such a separator in a battery includes the following steps: (1) providing a battery including an X-ray sensitive battery separator; (2) subjecting the battery to X-ray radiation; and (3) thereby detecting the position of said separator in said battery.

At least selected embodiments of the present invention relate to dry-stretch X-ray sensitive or detectable battery separators and to dry-stretch methods for making and methods of using such separators, including methods for detecting the position of such a separator in a battery, cell, stack, jellyroll, can, or the like.

At least selected embodiments of the present invention relate to wet process X-ray sensitive or detectable battery separators and to wet process methods for making and methods of using such separators, including methods for detecting the position of such a separator in a battery, cell, stack, jellyroll, can, or the like.

At least selected embodiments of the present invention relate to particle stretch X-ray sensitive or detectable battery separators and to particle stretch methods for making and methods of using such separators, including methods for detecting the position of such a separator in a battery, cell, stack, jellyroll, can, or the like.

At least selected embodiments of the present invention relate to modified dry-stretch X-ray sensitive or detectable battery separators and to modified dry-stretch methods for making and methods of using such separators, including methods for detecting the position of such a separator in a battery, cell, stack, jellyroll, can, or the like.

BRIEF DESCRIPTION OF THE DRAWINGS

For the purpose of illustrating the invention, there is shown in the drawings a form that is presently preferred; it being understood, however, that this invention is not limited to the precise embodiments, arrangements and instrumentalities shown.

DETAILED DESCRIPTION OF THE INVENTION

Figure 1:
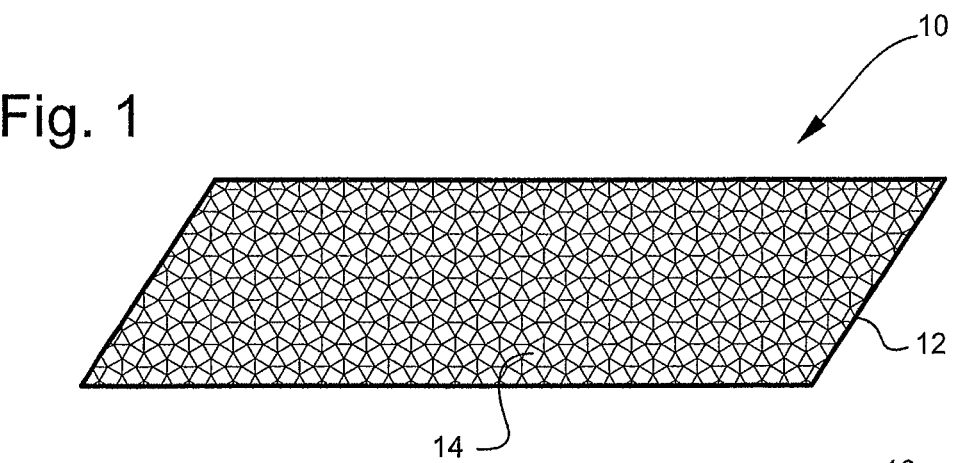
FIG. 1 is a schematic perspective view of a first embodiment of an X-ray sensitive battery separator according to the instant invention.

Referring to the drawings wherein like numerals indicate like elements, there is shown, in FIG. 1, a first embodiment of an X-ray sensitive battery separator 10. The X-ray sensitive battery separator 10 includes a microporous membrane 12, which contains an X-ray detectable element 14 dispersed therethrough.

Microporous membrane 12 may be any microporous membrane which contains X-ray detectable element 14. Microporous membranes are generally known in the art. Microporous membrane 12 may be made from any material, for example a polymer. A polymer, for example, may be any synthetic polymer, cellulose, or synthetically modified cellulose. The preferred synthetic polymers are polyolefins, e.g., polyethylene (PE), polypropylene (PP), polymethylpentene, polybutylene, ultra high molecular weight polyethylene, ultra high molecular weight polypropylene, copolymers thereof, and mixtures or blends thereof. Microporous membrane 12 may have any porosity; for example, microporous membrane 12 may have a porosity in the range of about 20% to about 80%. Microporous membrane 12 may have any average pore size; for example, microporous membrane 12 may have an average pore size in the range of about 0.1 micron to about 5 microns. Microporous membrane 12 may be made of one or more plies and may have any thickness; for example, microporous membrane 12 may have a thickness in the range of about 6 microns to about 80 microns.

X-ray detectable element 14 may be any X-ray detectable material. For example, X-ray material 14 may be a material selected from the group consisting of a metal oxide, a metal phosphate, a metal carbonate, an X-ray fluorescent material, a metal sulfate or salt such as barium sulfate ($BaSO_4$), and combinations thereof. The listed X-ray materials are not limiting. Exemplary metal oxides include, but are not limited to, metal oxides having a metal selected from the group consisting of Zn, Ti, Mn, Ba, Ni, W, Hg, Si, Cs, Sr, Ca, Rb, Ta, Zr, Al, Pb, Sn, Sb, Cu, Ni, and Fe. The listed metal oxides are not limiting. Exemplary metal phosphates include, but are not limited to, phosphate oxides having a metal selected from the group consisting of Zn, Ti, Mn, Ba, Ni, W, Hg, Si, Cs, Sr, Ca, Rb, Ta, Zr, Al, Pb, Sn, Sb, Cu, Ni, and Fe. The listed metal phosphates are not limiting. Exemplary metal carbonates include, but are not limited to, metal carbonates having a metal selected from the group consisting of Zn, Ti, Mn, Ba, Ni, W, Hg, Si, Cs, Sr, Ca, Rb, Ta, Zr, Al, Pb, Sn, Sb, Cu, Ni, and Fe. The listed metal carbonates are not limiting. Exemplary X-ray fluorescent materials include, but are not limited to, organic materials, inorganic materials, and combinations thereof. A fluorescent material, as used herein, refers to a material having electrons capable of becoming exited by X-ray radiation thereby providing detection signals. The listed X-ray fluorescent materials are not limiting. X-ray detectable element 14 may constitute any percentage of the weight of membrane 12. For example, the X-ray detectable element may constitute in the range of 0.01 to 98 percent by weight of the membrane 12, possibly preferably less than 20 percent by weight of the membrane 12, more preferably less than 15 percent by weight of the membrane 12, and most preferably less than 10 percent by weight of the membrane 12. When barium sulfate particles are used as an x-ray detectable element, in one possibly preferred embodiment, the barium sulfate is less than 10 percent by weight of the membrane 12, possibly more preferably between 2 and 5 percent by weight of the membrane 12, and possibly most preferably about 4 percent by weight of the membrane 12.

Figure 2:
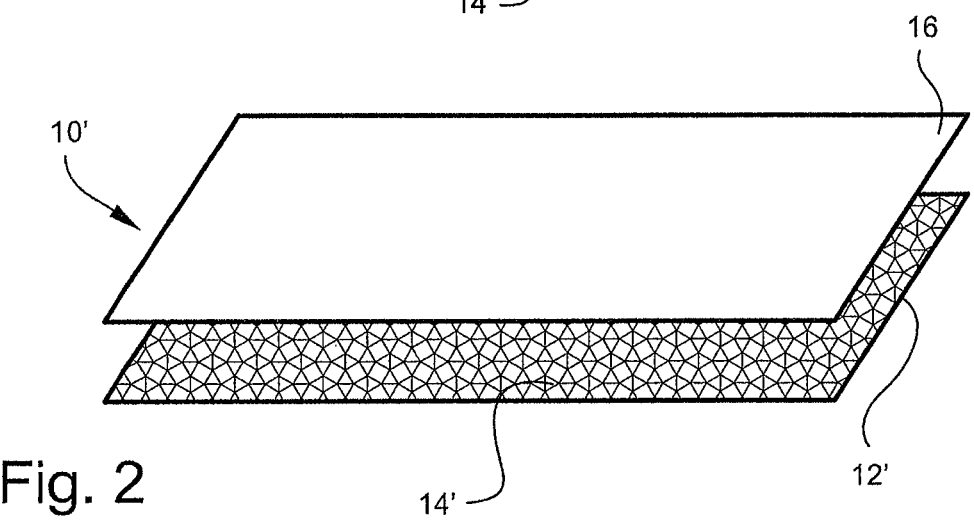
FIG. 2 is a schematic perspective view of second embodiment of an X-ray sensitive battery separator according to the instant invention.

In the alternative, referring to FIG. 2, the X-ray sensitive battery separator 10' may be a multi-layer battery separator. Multi-layer, as used herein, refers to two or more layers. The X-ray detectable battery separator 10' preferably includes at least one microporous membrane or layer 12', which contains an X-ray detectable element 14', and at least one other porous membrane, material or layer 16. Preferably, the X-ray sensitive or detectable battery separator 10' includes a plurality of layers 16, for example, one on each side of layer 12'. In one embodiment, the layer 16 is an additional layer 12'. Further, at least one of layers 16 or 12' or an additional layer may be a shutdown layer, i.e., one adapted to shut down ionic flow between the electrodes in the event of thermal runaway or internal short circuiting caused by internal or external circumstances.

Microporous membrane or layer 12' (or layers 12') may be any microporous membrane which contains X-ray detectable element 14'. Microporous membranes are generally known in the art. Microporous membrane 12' may be made from any material, for example a polymer. A polymer, for example, may be any synthetic polymer, cellulose, or synthetically modified cellulose. The preferred synthetic polymers are polyolefins, e.g., polyethylene (PE), polypropylene (PP), polymethylpentene, polybutylene, ultra high molecular weight polyethylene (UHMWPE), ultra high molecular weight polypropylene (UHMWPP), copolymers thereof, and mixtures or blends thereof. Microporous membrane 12' may have any porosity; for example, microporous membrane 12' may have a porosity in the range of about 20% to about 80%. Microporous membrane 12' may have any average pore size; for example, microporous membrane 12' may have an average pore size in the range of about 0.1 micron to about 5 microns. Microporous membrane 12' may be made of one or more plies and have any thickness; for example, microporous membrane 12' may have a thickness in the range of about 6 microns to about 80 microns.

X-ray detectable element 14' (like element 14) may be any X-ray detectable material. For example X-ray material 14' may be a material selected from the group consisting of a metal oxide, a metal phosphate, a metal carbonate, and an X-ray fluorescent material, a metal sulfate or salt such as barium sulfate ($BaSO_4$), and combinations thereof. The listed X-ray sensitive or detectable materials are not limiting. Exemplary metal oxides include, but are not limited to, metal oxides having a metal selected from the group consisting of Zn, Ti, Mn, Ba, Ni, W, Hg, Si, Cs, Sr, Ca, Rb, Ta, Zr, Al, Pb, Sn, Sb, Cu, Ni, and Fe. The listed metal oxides are not limiting. Exemplary metal phosphates include, but are not limited to, phosphate oxides having a metal selected from the group consisting of Zn, Ti, Mn, Ba, Ni, W, Hg, Si, Cs, Sr, Ca, Rb, Ta, Zr, Al, Pb, Sn, Sb, Cu, Ni, and Fe. The listed metal phosphates are not limiting. Exemplary metal carbonates include, but are not limited to, metal carbonates having a metal selected from the group consisting of Zn, Ti, Mn, Ba, Ni, W, Hg, Si, Cs, Sr, Ca, Rb, Ta, Zr, Al, Pb, Sn, Sb, Cu, Ni, and Fe. The listed metal carbonates are not limiting. Exemplary X-ray fluorescent materials include, but are not limited to, organic materials, inorganic materials, and combinations thereof. A fluorescent material as used herein refers to a material having electrons capable of becoming exited by X-ray radiation thereby providing detection signals. The listed X-ray fluorescent materials are not limiting. X-ray detectable element 14' may constitute any percentage of the weight of membrane 12'. For example, the X-ray detectable element 14' may constitute in the range of 0.01 to 98 percent by weight of the separator 10' or membrane 12', possibly preferably less than 20 percent by weight of the membrane 12', more preferably less than 15 percent by weight of the membrane 12', and most preferably less than 10 percent by weight of the membrane 12'. When barium sulfate particles are used as an x-ray detectable element, in one possibly preferred embodiment, the barium sulfate is less than 10 percent by weight of the membrane 12', possibly more preferably between 2 and 5 percent by weight of the membrane 12', and possibly most preferably about 4 percent by weight of the membrane 12'.

Layer or layers 16 may be any conventional porous or microporous membrane, material or layer. Porous or microporous membranes or materials are generally known in the art. Layer or layers 16 may be made from any material, for example a polymer. A polymer, for example, may be any synthetic polymer, cellulose, or synthetically modified cellulose. The preferred synthetic polymers are polyolefins, e.g., polyethylene (PE), polypropylene (PP), polymethylpentene, polybutylene, ultra high molecular weight polyethylene, ultra high molecular weight polypropylene, copolymers thereof, and mixtures or blends thereof. Layer 16 may have any porosity; for example, layer 16 may have a porosity in the range of about 20% to about 80%. Layer 16 may have any average pore size; for example, layer 16 may have an average pore size in the range of about 0.1 micron to about 5 microns. Layer 16 may be made of one or more plies and have any thickness; for example, layer 16 may have a thickness in the range of about 10 microns to about 40 microns. When separator 10' includes more than one layer 16, each such layer 16 may be of the same or different construction. As non-limiting examples, separator 10' may have a PP layer 12' and a PP layer 16, a PP layer 12' and a PE layer 16, a PE layer 12' and a PP layer 16, a PE layer 12' and a PE layer 16, a PE layer 12' between two like PP layers 16, a PE layer 12' between two different PP layers 16, a PP layer 12' between two like PE layers 16, a PP layer 12' between two different PE layers 16, a PE layer 12' between a first PP layer 16 and a second PE layer 16, two PP layers 12', two PP layers 12' and a PE layer 16, two PE layers 12', two PE layers 12' between two PP layers 16, or the like. Layers 12' and 16 of separator 10', may, for example, be coextruded, laminated, or bonded together.

Figure 3:
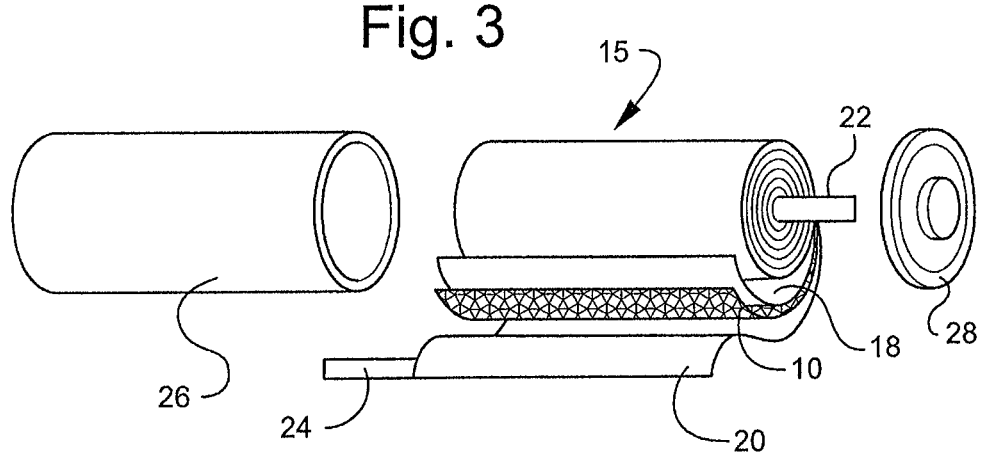
FIG. 3 is an exploded view of a battery or can including the X-ray sensitive battery separator of FIG. 1.

In manufacturing, referring to FIG. 3, the X-ray sensitive battery separator 10 of FIG. 1 (or 10' of FIG. 2), is sandwiched between a positive electrode 18 and a negative electrode 20, and may be subsequently rolled into a jellyroll 15 (prismatic constructions or stacks, rectangular cells, pocket cells, button cells, other cans, containers, constructions, or the like, are also possible). The jellyroll 15 may further include negative tab 24, and positive tab 22. Positive electrode 18 may include a metal sheet, e.g., aluminum foil, i.e. the current collector, upon which the positive electrode material or electrode active mix (not shown but conventional) has been spread in conventional manner. Negative electrode 20 may include a metal sheet, e.g., copper foil, i.e. the current collector, upon which the negative electrode material or electrode active mix (not shown but conventional) has been spread in conventional manner. Subsequently, jellyroll 15 is inserted into can 26, which is filled with an electrolyte (not shown), and then, can 26 is sealed with cap 28 (or with a cap at each end). Can 26 may be a metallic (e.g., steel, stainless steel, aluminum) cylindrical can, a plastic box, of a foil (e.g., metallized foil) pouch, or the like. Electrolyte may be any substance capable of providing ionic conductivity. Electrolyte may, for example, be a liquid electrolyte, a solid electrolyte, or a polymer or gel electrolyte. A liquid electrolyte generally includes an electrolytic salt dissolved in a solvent, i.e. an inorganic solvent or an organic solvent. A gel electrolyte generally includes an electrolytic salt dissolved in non-aqueous solvent, and gelated with a polymer matrix.

In operation, a battery, cell, stack, jellyroll, can, or the like containing an X-ray sensitive battery separator 10 (or 10') is subjected to X-ray radiation thereby facilitating the detection of the position of the X-ray sensitive battery separator 10 (or 10') within the battery, cell, stack, jellyroll, can, or the like. For example, the separator is usually wider than the electrodes, so that the separator extends beyond the lateral edges of the electrodes. The separator separates and extends beyond the lateral edges of the electrodes to prevent the electrodes from coming into physical contact and thereby creating the potential for short-circuiting. It is possible that during winding or in the battery assembly that the separator portion that extends beyond the lateral edges of the electrodes is removed, shifted or pushed back or otherwise misplaced (or the electrodes are moved or misplaced) thereby allowing the possibility of physical contact of the electrodes. An X-ray examination of the assembled battery, cell, stack, or the like allows a check, inspection or test to determine that the separator remains (or electrodes remain) in position throughout manufacture. The X-ray visible separator can be observed, via X-ray examination, to ensure that it has maintained its position (i.e., a portion extending beyond the lateral edges of the electrodes). Further, it is possible that the x-ray inspection process could be automated, via computer, to increase the speed of inspection.

In accordance with at least selected possibly preferred embodiments, the membranes or layers 12, 12', and/or 16 are made by the dry-stretch process (the CELGARD process) where pore formation results from stretching a nonporous, semicrystalline, extruded polymer precursor in the machine direction (MD stretch). See, for example, Kesting, Ibid. pages 290-297, incorporated herein by reference. Such a dry-stretch process is different from the wet process and the particle stretch process.

In accordance with at least other selected possibly preferred embodiments, the membranes or layers 12, 12', and/or 16 are made by the wet process, also known as the phase inversion process, the extraction process, or the TIPS process, where the polymeric raw material is mixed with a processing oil (sometimes referred to as a plasticizer), this mixture is extruded, and pores are then formed when the processing oil is removed (these films may be stretched before or after the removal of the oil). See, for example, Kesting, Ibid. pages 237-286, incorporated herein by reference.

In accordance with at least still other selected possibly preferred embodiments, the membranes or layers 12, 12', and/or 16 are made by the particle stretch process, where the polymeric raw material is mixed with pore forming particulate, this mixture is extruded, and pores are formed during stretching when the interfaces between the polymer and the particulate fracture due to the stretching forces. See, for example, U.S. Pat. Nos. 6,057,061 and 6,080,507, each incorporated herein by reference.

In accordance with at least yet other selected possibly preferred embodiments, the membranes or layers 12, 12', and/or 16 are made by a modified dry-stretch process (modified CELGARD process) involving, for example, stretching a nonporous, semicrystalline, extruded polymer precursor in the machine direction (MD stretch), followed by stretching in the transverse direction (TD stretch) with machine direction relax (MD relax). See, for example, US Published Application US2007/0196638 A1, published Aug. 23, 2007, and incorporated by reference herein.

In accordance with at least still yet other selected embodiments, the membranes or layers 12, 12', and/or 16 are polypropylene microporous membranes, made from a beta-nucleated precursor, or beta-nucleated polypropylene (BNPP) as disclosed, for example, in U.S. Pat. No. 6,368,742, incorporated herein by reference. A beta-nucleating agent for polypropylene is a substance that causes the creation of beta crystals in polypropylene.

Further, in place of or in addition to the x-ray detectable element 14 or 14' being incorporated into the membrane or layer 12, 12', or 16, by, for example, being mixed with the polymer prior to extrusion or formation of the precursor, membrane, film, or the like, the x-ray detectable element 14 or 14' may be applied to the membrane or layer 12, 12', or 16, to the precursor of membrane or layer 12, 12', or 16, may be coated on the membrane or layer 12, 12', or 16, may be applied to the membrane or layer 12, 12', or 16, or the like. For example, but not limited to, barium sulfate particles may be incorporated into the membrane or layer 12, 12', or 16, by being mixed with the polymer mix prior to extrusion or formation of the precursor, membrane, film, or the like, may be applied to the membrane or layer 12, 12', or 16, or to the precursor of membrane or layer 12, 12', or 16, may be coated on the membrane or layer 12, 12', or 16, or may be coated on the precursor of the membrane or layer 12, 12', or 16, or the like. In this way, the x-ray detectable element or elements 14 or 14' may be incorporated into, on the surface of, applied to, and/or in the pores of the membrane or layer 12, 12', and/or 16. For example, but not limited to, the X-ray detectable element 14 or 14' may be incorporated into, on the surface of, applied to, and/or in the pores of the membrane or layer 12 or 12', and may constitute any percentage of the weight of membrane 12 or 12' or of separator 10 or 10'. For example, the X-ray detectable element 14 or 14' may constitute in the range of 0.01 to 98 percent by weight of the separator 10 or 10' or membrane 12 or 12', preferably less than 20 percent by weight of the membrane 12 or 12', more preferably less than 15 percent by weight of the membrane 12 or 12', and most preferably less than 10 percent by weight of the membrane 12 or 12'. When barium sulfate particles are used as an x-ray detectable element, in one possibly preferred embodiment, the barium sulfate is less than 10 percent by weight of the separator 10 or 10' or of the membrane 12 or 12', possibly more preferably between 2 and 5 percent by weight of the membrane 12 or 12', and possibly most preferably about 4 percent by weight of the membrane 12 or 12'. When barium sulfate particles are used as an x-ray detectable element, in another possibly preferred embodiment, the barium sulfate is less than 15 percent by weight of the precursor of the membrane 12 or 12', possibly more preferably less than 10 percent by weight of the precursor, possibly preferably between 1 and 10 percent by weight of the precursor, and possibly most preferably about 7 to 8 percent by weight of the precursor.

In one possible example, a porous polymer membrane 12 has a coating including barium sulfate particles and a binder on one surface thereof. The weight percent of barium sulfate is preferably less than 20% by weight of the combined membrane and coating weight.

In accordance with at least selected embodiments of the present invention, there is provided an X-ray sensitive battery separator for a secondary lithium battery and a method for detecting the position of such a separator in a secondary lithium battery. In accordance with at least selected embodiments, the preferred X-ray sensitive battery separator includes a microporous membrane having an X-ray detectable element. In accordance with at least selected embodiments, the X-ray detectable element constitutes a sufficient amount to detect the separator relative to the electrodes (for example, to provide minimum contrast in the x-ray picture). In accordance with at least particular separator embodiments, the X-ray detectable element constitutes less than 20% by weight of the microporous membrane, preferably less than 15% by weight of the microporous membrane, more preferably less than 10% by weight of the microporous membrane, and most preferably less than 5% by weight of the microporous membrane.

At least an exemplary method for detecting the position of a separator in a battery, cell, stack, jellyroll, can, or the like, includes the following steps: (1) providing a battery, cell, stack, jellyroll, can, or the like including an X-ray sensitive or detectable battery separator; (2) subjecting the battery, cell, stack, jellyroll, can, or the like to X-ray radiation; and (3) thereby detecting the position of the separator in the battery, cell, stack, jellyroll, can, or the like.

In accordance with at least selected embodiments of the present invention, there are provided improved battery separators, methods, or the like, such as an improved battery separator which is x-ray sensitive or readily detectable when embedded in a battery, cell, stack, jellyroll, can, or the like, to determine its position within the battery, cell, stack, jellyroll, can, or the like, or to determine its position relative to the electrodes, which is relatively easy to manufacture, is low cost, meets performance requirements, meets product specifications, and/or the like. Furthermore, in accordance with at least selected embodiments of the present invention, there are provided improved methods for making, using, or detecting the position of a separator in a battery, cell, stack, jellyroll, can, or the like, such as an improved battery separator which is x-ray sensitive or readily detectable, to determine its position within the battery, cell, stack, jellyroll, can, or the like, or relative to the electrodes, which is relatively easy and cost effective, for manufacturing such a separator which is relatively simple and cost effective, for using such a separator which is relatively simple and cost effective, and/or the like.

In accordance with at least certain embodiments, the instant application relates to an X-ray sensitive battery separator for a secondary lithium battery and a method for detecting the position of such a separator in a secondary lithium battery. The X-ray sensitive battery separator preferably includes a microporous membrane having an X-ray detectable element. The X-ray detectable element, such as barium sulfate particles, preferably constitutes less than 5% by weight of the microporous membrane. The method for detecting the position of such a separator in a battery includes the following steps: (1) providing a battery including an X-ray sensitive battery separator; (2) subjecting the battery to X-ray radiation; and (3) thereby visually detecting the position of said separator in said battery.

At least selected embodiments of the present invention relate to dry-stretch X-ray sensitive or detectable battery separators and to dry-stretch methods for making and methods of using such separators, including methods for detecting the position of such a separator in a battery, cell, stack, jellyroll, can, or the like.

At least selected embodiments of the present invention relate to wet process X-ray sensitive or detectable battery separators and to wet process methods for making and methods of using such separators, including methods for detecting the position of such a separator in a battery, cell, stack, jellyroll, can, or the like.

At least selected embodiments of the present invention relate to particle stretch X-ray sensitive or detectable battery separators and to particle stretch methods for making and methods of using such separators, including methods for detecting the position of such a separator in a battery, cell, stack, jellyroll, can, or the like.

At least selected embodiments of the present invention relate to modified dry-stretch X-ray sensitive or detectable battery separators and to modified dry-stretch methods for making and methods of using such separators, including methods for detecting the position of such a separator in a battery, cell, stack, jellyroll, can, or the like.

At least selected embodiments relate to an X-ray sensitive battery separator for a secondary lithium battery and a method for detecting the position of a separator in a secondary lithium battery, an X-ray sensitive battery separator including at least one microporous membrane having an X-ray detectable element therein, thereon, or added thereto, an X-ray detectable element constituting less than 20% by weight of the microporous membrane or separator, and/or a method for detecting the position of a separator in a battery, cell, stack, jellyroll, can, or the like includes the following steps: (1) providing a battery, cell, stack, jellyroll, or the like including an X-ray sensitive battery separator; (2) subjecting the battery, cell, stack, jellyroll, or the like to X-ray radiation; and (3) thereby detecting the position of said separator in said battery, cell, stack, jellyroll, or the like.

The present invention may be embodied in other forms without departing from the spirit and the essential attributes thereof, and, accordingly, reference should be made to the appended claims, rather than to the foregoing specification, as indicated the scope of the invention.

We claim:

1. A method for detecting the position of a separator relative to electrodes in a secondary lithium battery comprising the steps of:

providing a secondary lithium battery including a positive electrode, a negative electrode, a X-ray sensitive separator located between the electrodes, and a can or pouch housing the electrodes and separator, the X-ray sensitive separator comprising a microporous membrane having a X-ray detectable element dispersed therein or thereon, the X-ray detectable element comprising at least 2 and no greater than 20 weight % of the membrane;

subjecting the secondary lithium battery to X-ray radiation;

determining the position of the separator relative to the electrodes; and approving or rejecting the secondary lithium battery based upon the position of the separator relative to the electrodes.

2. The method of claim 1 wherein the X-ray detectable element comprising 2 to 10 weight % of the membrane.

3. The method of claim 1 wherein the X-ray detectable element comprising 2 to 5 weight % of the membrane.

4. The method of claim 1 wherein the X-ray detectable element comprising about 4 weight % of the membrane.

5. The method of claim 1 wherein the X-ray detectable element being selected from the group consisting of metal, metal oxide, metal phosphate, metal carbonate, X-ray fluorescent material, metal salt, metal sulfate, or mixtures thereof, and any of the foregoing metals being selected from the group consisting of Zn, Ti, Mn, Ba, Ni, W, Hg, Si, Cs, Sr, Ca, Rb, Ta, Zr, Al, Pb, Sn, Sb, Cu, Fe, and mixtures thereof.

6. The method of claim 1 wherein the X-ray detectable element being barium sulfate.

7. The method of claim 1 wherein the X-ray detectable element is in a coating on the membrane.

8. The method of claim 7 wherein the coating is a ceramic coating.

9. The method of claim 8 wherein the X-ray detectable element being barium.

10. The method of claim 1 wherein the X-ray detectable element is at least one of dispersed therein, coated thereon, or added thereto.

* * * * *